United States Patent [19]

Wallace

[11] Patent Number: 5,112,975
[45] Date of Patent: May 12, 1992

[54] PREPARATION OF NOROXYMORPHONE FROM MORPHINE

[75] Inventor: Rebecca A. Wallace, Manchester, Mo.

[73] Assignee: Mallinckrodt Specialty Chemicals Company, St. Louis, Mo.

[21] Appl. No.: 406,988

[22] Filed: Sep. 14, 1989

Related U.S. Application Data

[63] Continuation-in-part of Ser. No. 196,539, Jul. 18, 1988, abandoned, which is a continuation of Ser. No. 863,209, May 14, 1986, abandoned, which is a continuation of Ser. No. 713,932, Mar. 10, 1985, abandoned, which is a continuation-in-part of Ser. No. 593,744, Mar. 27, 1984, abandoned.

[51] Int. Cl.⁵ .................. C07D 489/08; C07D 489/02
[52] U.S. Cl. ............................................ 546/45; 546/44
[58] Field of Search .................................. 546/44, 45

[56] References Cited

U.S. PATENT DOCUMENTS

| | | | |
|---|---|---|---|
| 2,772,270 | 11/1956 | Weiss | 546/45 |
| 3,332,950 | 7/1967 | Blumberg et al. | 546/45 |
| 3,905,981 | 9/1975 | Olofson et al. | 546/45 |
| 4,451,470 | 5/1984 | Ganti | 546/44 X |
| 4,472,253 | 9/1984 | Schwartz | 204/158 R |
| 4,639,520 | 1/1987 | Kavka | 546/45 |
| 4,795,813 | 1/1989 | Schwartz | |

FOREIGN PATENT DOCUMENTS

| | | |
|---|---|---|
| 2515184 | 4/1983 | France . |
| 8203204 | 3/1983 | Netherlands . |
| 1260699 | 1/1972 | United Kingdom . |

OTHER PUBLICATIONS

Schwartz & Wallace, "Efficient Synthesis of 14-Hydroxymorphinans from Codeine" *J. Med. Chem.* (1981), 24, pp. 1525-1528.

Hauser et al., "14-Hydroxycodeinone, An Improved Synthesis", *J. Med. Chem.*; (1974), vol. 17, No. 10, p. 1117.

Iijima, Rice & Brossi, "The Oxidation of Thebaine with m-Chloroperbenzoic Acid " *Helv. Chim. Acta* (1977), vol. 60, Fasc. 7 Nr. 213, pp. 2135-37

Kirk & Wiles, "The Reaction of m-Chloroperbenzoic Acid with 3-Acetoxy-steroidal 3,5-Dienes," *Chem. Comm.* (1970), p. 518.

Kirk & Wiles, "Competing Reactions in the Peroxyacid Oxidation of 3-Alkoxy-steroidal 3,5-Dienes," *Chem. Comm.* (1970), pp. 5015-1016.

Bentley, *The Chemistry of the Morphine Alkaloids*, 1954, pp. 251, 252 & 262.

Olofson et al., Tetrahedron Letters, No. 19, pp. 1571-1574 (1977).

Rice et al.; Heterocyclic Chem., vol. 14, pp. 665-666 (1977).

Rice et al., J. Med. Chem., vol. 18, No. 10, pp. 1033-1035 (1975).

Greene, T. W., Protective groups in Organic Synthesis, pp. 88-92, 104-105, 293-294, and 307-310.

Fieser, et al., "Reagents for Organic Synthesis", John Wiley & Sons, Inc., New York, (1967), pp. 144-147.

McOmie, "Protective Groups in Organic Chemistry", Plenum Press, London (1973) pp. 55-56.

*Primary Examiner*—Diana Rivers
*Attorney, Agent, or Firm*—Rothwell, Figg, Ernst & Kurz

[57] ABSTRACT

3,17-(diethoxycarbonyl)normorphine, which may be prepared by reaction of morphine with ethyl chloroformate, is converted to 3,17-(diethoxycarbonyl)normorphinone, a novel compound, by oxidation. The novel normorphinone derivative is converted to 3,17-(diethoxycarbonyl)normorphinone enol acetate, a second novel compound, by esterification with acetic anhydride or acetyl halide.

A 14-hydroxy group is introduced into the novel dienol ester by oxidation with peracid. The resultant 14-hydroxy-3,17-(diethoxycarbonyl)normorphinone, a third novel compound, may be catalytically hydrogenated to produce 3,17-(diethoxycarbonyl)noroxymorphone. The latter intermediate may be converted to noroxymorphone by hydrolysis.

18 Claims, No Drawings

PREPARATION OF NOROXYMORPHONE FROM MORPHINE

This application is a continuation-in-part of application Ser. No. 196,539, filed Jul. 18, 1988, now abandoned, which was a continuation of application Ser. No. 863,209, filed May 14, 1986, now abandoend, which was a continuation of application Ser. No. 713,932, filed Mar. 20, 1985, now abandoned, which was a continuation-in-part of application Ser. No. 593,744, filed Mar. 27, 1984, now abandoned, which is incorporated herein by reference.

FIELD OF THE INVENTION

This invention relates to a process for preparing noroxymorphone from morphine in high yields.

BACKGROUND OF THE INVENTION

14-Hydroxymorphinans, including such "nal" compounds as naloxone, naltrexone, and nalbuphine are important morphine derivatives due to their behavior as potent analgesics and/or narcotic antagonists. See U.S. Pat. No. 3,254,088 (naloxone); U.S. Pat. No. 3,332,950 (naltrexone); and U.S. Pat. No. 3,393,197 (nalbuphine). Among the prior synthetic routes to the preparation of these pharmaceuticals have been processes which utilize thebaine as a starting material. However, thebaine-based syntheses are not entirely satisfactory for a number of reasons. For example, thebaine is in limited supply and its cost is high, thereby contributing to high cost of the noroxymorphone and the 14-hydroxymorphinans derived from it.

Because of the scarcity and high cost of thebaine, efforts have been made in the art to devise methods for the synthesis of noroxymorphone from compounds in more plentiful supply than thebaine, for example morphine.

To synthesize noroxymorphone from morphine, the tertiary amine at the 17 position must be converted to a secondary amine via demethylation by some method; a hydroxyl group must be introduced at the 14 position; the hydroxyl group at the 6 position must be converted to a ketone; and the cycloalkene double bond must be reduced. However, the 3-hydroxyl group must survive the multiple reaction and purification steps and so must be protected. The protective group must be substantially uneffected by the reactions necessary to carry out these conversions, including extremely low pH reaction conditions, for example, less than 1.0 in one step. Yet the protecting group must be easily removable to restore the hydroxyl group when desired.

Moreover, all of these reactions, whether converting or protecting, must each be capable of producing high yields so that the overall yield of the multistep synthesis will be relatively high and the economics of producing noroxymorphone will not be adversely affected.

The present invention supplies these needs. It has been found that the 3-hydroxyl group, which is phenolic, can be protected by a carbonate, which will, surprisingly, survive the multiple reaction steps necessary to complete the conversion. It has been heretofore reported that carbonates provided only "marginal" protection to phenolic hydroxyl groups when exposed to pH conditions of less than 1. (See Greene, Protective Groups in Organic Synthesis.) However, in the present invention a carbonate group does protect the 3 position hydroxyl group under such conditions.

Advantageously, the same reaction that adds the carbonate to the 3 position produces a carbamate protecting group at the 17 position from the secondary amine, thus fulfilling two needs through one reaction. Additionally, the reaction step does not affect, to any substantial degree, the second hydroxyl group, so it can later be converted to a ketone. This advantageous discovery allows for a novel, economical route to synthesize noroxymorphone, in which a 14-hydroxyl group can be introduced using a peracid.

SUMMARY OF THE INENTION

Generally stated, the present invention provides a process for preparing noroxymorphone from morphine by the following steps:

(1) converting morphine to 3,17-(di-$R_1$-oxycarbonyl)-normorphine (also hereinafter formula J), (2) converting the 3,17-(di-$R_1$-oxycarbonyl)normorphine to 3,17-(di-$R_1$-oxycarbonyl) normorphinone (also hereinafter formula K), (3) converting the 3,17-(di-$R_1$-oxycarbonyl) normorphinone to 3,17-(di-$R_1$-oxycarbonyl) normorphinone dienol acylate (also hereinafter formula L), (4) converting the dienol acylate to 14-hydroxy-3,17-(di-$R_1$-oxycarbonyl)normorphinone (also hereinafter formula M), (5) converting the 14-hydroxy-3,17-(di-$R_1$-oxycarbonyl)normorphino ne to 3,17-(di-$R_1$-oxycarbonyl)-noroxymorphone (also hereinafter formula N), and (6) converting the 3,17-(di-$R_1$-oxycarbonyl) noroxymorphone to noroxymorphone, wherein $R_1$ is an alkyl, alkenyl, aralkyl or aryl group such that the $R_1$-oxycarbonyl groups attached to the 3-O and 17-N atoms of the various intermediate compounds are alkyloxy, alkenyloxy, aralkyloxy or aryloxy groups.

The present invention also provides, as novel compositions of matter useful in the above process, the following compounds:

3,17-(di-$R_1$-oxycarbonyl)normorphinone, 3,17-(di-$R_1$-oxycarbonyl)normorphinone dienol acylate, and 14-hydroxy-3,17-(di-$R_1$-oxycarbonyl)normorphinone wherein $R_1$ is as defined above. The $R_1$-oxycarbonyl groups protect the hydroxy and amine functionalities of the morphine molecule as discussed above.

The invention also is directed to a process corresponding to Step 2 wherein such conversion is effected by reaction of the compound of formula J with an oxidizing agent effective for oxidizing allylic hydroxyl groups to keto groups, whereby the compound of formula K is prepared.

The invention is further directed to a process corresponding to Step 3 wherein such conversion is effected by reaction of the compound of formula K with an acid anhydride of the formula $(R_2)_2O$ or an acyl halide of the formula $R_2X$ where $R_2$ is an acyl group and X is halogen, whereby the dienol acylate compound of formula L is prepared.

The invention is still further directed to a process corresponding to Step 4 wherein such conversion is effected by reaction of the compound of formula L with a peracid under reaction conditions effective for substituting a hydroxyl group in the 14 position, whereby the 14-hydroxy-3,17-disubstituted-normorphinone compound of formula M is prepared.

DETAILED DESCRIPTION OF THE INVENTION

The overall process is illustrated by the Reaction Schematic below. In the formulas J, K, L, M and N shown in the Reaction Schematic, $R_1$ is as defined above and $R_2$ is an acyl group, with $R_1$ and $R_2$ preferably being an ethyl group and an acetyl group, respectively. The reaction steps correspond to those enumerated above.

$R_1$ is ethyl. Ethyl chloroformate is the preferred haloformate ester.

The reaction is preferably carried out under an inert atmosphere in the presence of an inert organic liquid medium (hereinafter referred to as an "organic solvent") in which the reactants can be dissolved or dispersed under the reaction conditions employed to form a solution, dispersion, suspension or other reaction mixture. As used herein, the modifying term "inert" means that the substance referred to in connection with an Reaction Schematic

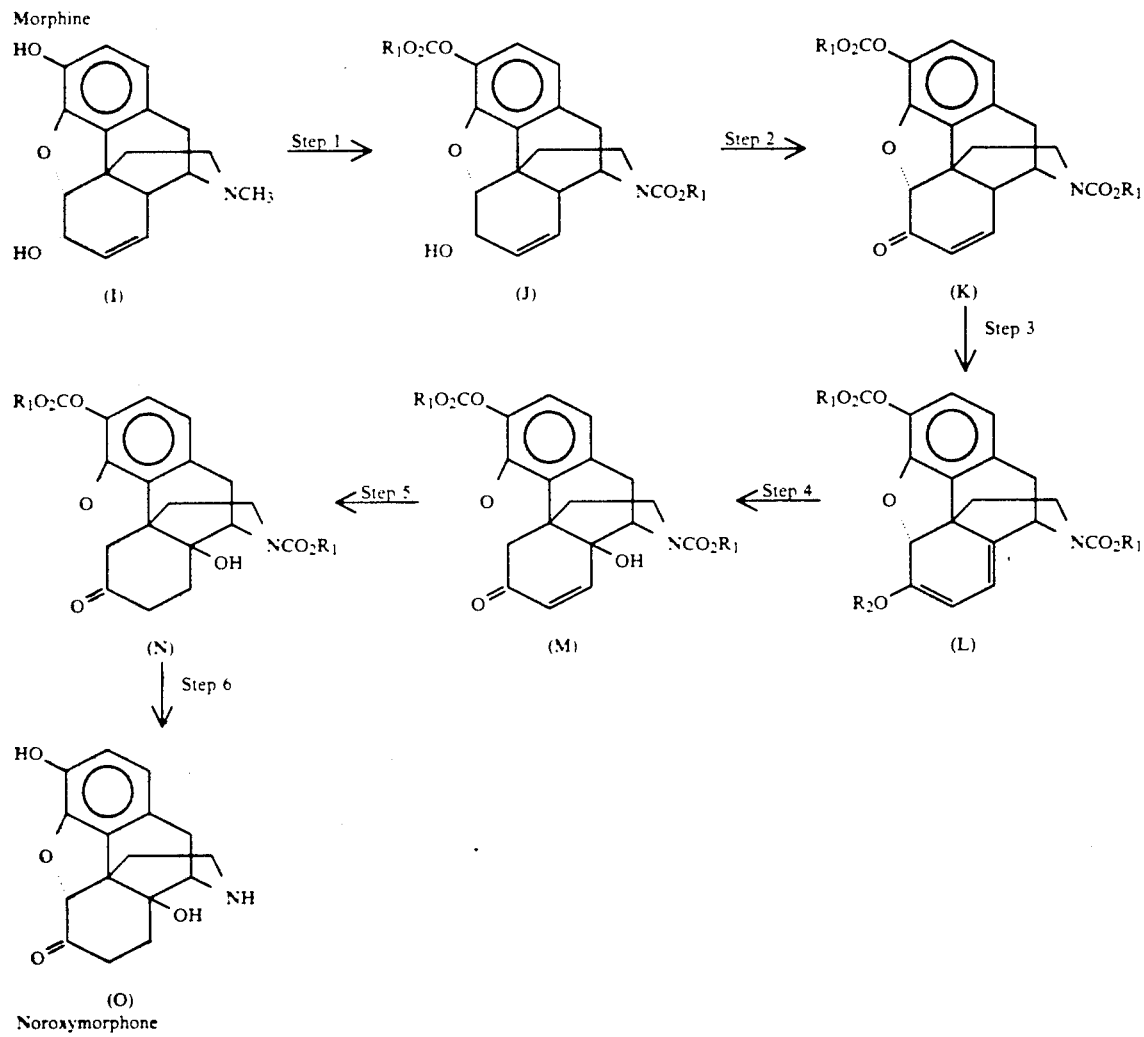

associated reaction is at least substantially nonreactive with the reactants and desired product or products.

Step 1. In the present method for preparing noroxymorphone from morphine, the initial step is conversion of morphine to the compound of formula J. This single reaction introduces both a carbonate protecting group for the 3-hydroxyl group and a carbonate protecting group for the secondary amine. This is produced by reacting morphine with, for example, a haloformate ester of the formula $X-C(=O)OR_1$ where X is a halogen, preferably bromine or chlorine or more preferably chlorine (whereby the haloformate ester is a chloroformate), and $R_1$ is as defined above. Illustrative $R_1$ groups within the above definition are methyl, ethyl, propyl, heptyl, 1,1,1-tri-chloroethyl, vinyl, butenyl, phenyl, benzyl, carbobenzyl and naphthyl groups. Preferably The haloformate ester is preferably added slowly to a solution or other mixture of morphine in the organic solvent employed, with stirring. The organic solvent may be, for example, an arene, ketone, ester, chlorinated alkane, chlorinated arene or a mixture of two or more of such organic solvents. Chloroform is preferred as the solvent.

The reaction is preferably promoted by the presence of a weak base which may be, for example, potassium bicarbonate, sodium bicarbonate, pyridine or substituted pyridine, triethylamine, imadazole, sodium carbonate, potassium carbonate or a mixture of two or more of such weak bases. Sodium bicarbonate is preferred. The weak base is preferably present in the mixture of morphine and organic solvent to which the haloformate ester is to be added.

Suitable conditions for the reaction in Step 1 include the addition or presence of, per mole of morphine: about 2-50 moles of the haloformate ester such as an alkyl, alkenyl, aralkyl, or aryl bromoformate or chloroformate (preferably about 7.8 moles of ethyl chloroformate), about 1-20 moles of weak base (preferably about 15 moles of sodium bicarbonate), and about 0.1-10 liters of organic solvent (preferably about 10 liters of chloroform). The reaction may suitably be effected at, for example, atmospheric pressure and a temperature of about 40°-120° C., while about 90°-100° C. is preferred. The inert atmosphere is preferably nitrogen.

Preferably the reaction mixture is substantially anhydrous, i.e., the mixture does not contain more than 5% water and more preferably not more than 1 to 2% water. Optimally, the reaction mixture is entirely free of water. Accordingly, the components used for preparing the reaction mixture are preferably at least substantially anhydrous. Water of hydration in morphine can be, and preferably is, removed by azeotropic distillation with toluene.

At the conclusion of the reaction the product, 3,17-(di-$R_1$-oxycarbonyl)normorphine, can be removed by cooling the reaction mixture (preferably to about 25° C.), and thereafter washing (e.g., by adding water at 25° C.), drying and evaporating the solvent.

The balance of this description, including conditions and parameters for Steps 2-6 set forth below of the process for preparing noroxymorphone from morphine, is given with principal reference to such steps and associated compounds produced therein for the case where Step 1 is carried out using an ethylhaloformate ester (e.g., ethychloroformate) and the acyl group ($R_2$) is acetyl by way of illustration. It is understood, however, that other $R_1$ and $R_2$ groups may be substituted in whole or in part for the ethyl and acetyl groups, respectively, in the balance of this description unless otherwise indicated.

Step 2. In the next step of the process for preparing noroxymorphone from morphine, oxidation of the compound of Formula J is effected by reactively contacting that compound with an oxidizing agent effective for oxidizing allylic hydroxyl groups to keto groups, thereby preparing 3,17-(di-$R_1$-oxycarbonyl)normorphinone. Suitable oxidizing agents include chromium oxidants (e.g., chromium trioxide, pyridinium dichromate and t-butyl ammonium dichromate); benzophenone and cyclohexanone, each preferably employed with a base; manganese dioxide; and mixtures of dimethylsulfoxide with acetic anhydride. Chromium trioxide is preferred and advantageously may be employed in glacial acetic acid, in pyridine, in a mixture of pyridine and methylene chloride, or in aqueous sulfuric acid. An especially preferred oxidizing agent is Jones Reagent, a solution of chromium trioxide in aqueous sulfuric acid. The use of this agent, as well as some others just mentioned, will produce a reaction medium having an extremely low pH. In the case of Jones Reagent, this was measured at less than 1.0.

The oxidation reaction is preferably carried out under an inert atmosphere in the presence of an inert organic liquid medium (hereinafter referred to as an "organic solvent") in which the reactants can be dissolved or dispersed under the reaction conditions employed to form a solution, dispersion, suspension or other reaction mixture. The organic solvent employed in the reaction of Step 2 is preferably acetone. The oxidizing agent is preferably added slowly to a solution or other mixture of the compound of Formula J in the organic solvent employed, with stirring.

Suitable conditions for the reaction in Step 2 include the addition or presence of, per mole of the compound of Formula J: about 0.7 to 6.0 moles of the oxidant or oxidizing agent (preferably about 1.1 moles of chromium trioxide as Jones Reagent) and about 0.1-10 liters of the organic solvent employed (preferably about 3.8 liters of acetone). The reaction may suitably be effected at, for example, atmospheric pressure and a temperature of about 0°-25° C., while about 0°-10° C. is preferred. The inert atmosphere is preferably nitrogen Anhydrous conditions are not required for Step 2. The product of Step 2, the compound of Formula K, can be recovered in any suitable manner.

Where, as preferred, the oxidant is chromium trioxide in the form of Jones Reagent, the reaction advantageously is quenched after completion of the reaction using any suitable quenching procedure. Preferably, an alcohol and base are added to the reaction mixture to aid in quenching, followed by decanting the resulting mixture, washing the residual solids with acetone, decanting the resulting decanted mixtures or solutions and evaporating at least a substantial portion of the acetone and alcohol from the combination to give the compound of Formula K in the form of an oil, which preferably is crystallized from anhydrous ethanol to improve the purity of the product. Isopropyl alcohol is preferably employed as the quenching alcohol, while sodium bicarbonate is preferred for the quenching base. These compounds have been found to be highly effective for neutralizing the reaction mixture containing Jones Reagent and facilitating recovery of larger amounts of higher purity compound K.

If desired, recovery of compound K from the reaction mixture may include a step of extraction of the quenched reaction mixture. Evaporation of the acetone solution should precede extraction. Such extraction advantageously is effected using an organic solvent which may be, for example, an arene, ketone, ester, chlorinated alkane or chlorinated arene capable of preferentially dissolving compound K and thereafter evaporating the extract solvent to yield an oil which can be crystallized as above to yield compound K in cryatalline form.

The compounds of Formula K are novel intermediates useful in the synthesis of noroxymorphone in accordance with this invention.

Step 3. In the next step of the process for preparing noroxymorphone from morphine, acylation of the compound of Formula K is effected by reactively contacting that compound with an acylating agent which is an acid anhydride of the formula $(R_2)_2O$ or an acyl halide of the formula $R_2X'$ where $R_2$ is as defined above and $X'$ is halogen, whereby the dienol acylate compound of Formula L is prepared. Preferably, $X'$ is bromide or more preferably chloride, and $R_2$ is acetyl.

The acetylation or other acylation reaction is preferably carried out under an inert atmosphere in the presence of a catalytic acid (hereinafter referred to as an "acid catalyst") or more preferably in the presence of a catalytic base (hereinafter referred to as a "base catalyst").

Suitable conditions for the reaction in Step 3 include the addition or presence of, per mole of the compound of Formula K: about 0.01 to 5.0 moles of base (i.e., base catalyst) and about 1-100 moles of acylating agent. The reaction may suitably be effected at, for example, atmospheric pressure and a temperature of about 25°-140° C., while about 100°-105° C. is preferred. The inert is preferably nitrogen. Anhydrous conditions substantially as described above for Step 1 are preferred.

Suitable acylating agents include, for example, acetyl chloride and mixed anhydrides of acetic acid. Acetic anhydride is preferred. The base catalyst may be, for example, sodium or potassium acetate, pyridine, triethylamine or mixtures of two or more of the foregoing bases. Sodium acetate is generally preferred as the catalyst, especially where the preferred acylating agent (acetic anhydride) is employed. Suitable acid catalysts include, for example, p-toluene sulfonic acid and boron trifluoride etherate. The conditions and parameters set forth above for Step 3 are generally applicable for use with the various $R_1$ and $R_2$ groups within the above definitions.

Preferably, per mole of a compound of Formula K, there are employed about 1.0 moles of preferably anhydrous sodium acetate and about 19.8 moles of acetic anhydride, which also functions as a solvent.

At the conclusion of the reaction, which may be completed within, for example, about two hours, the 3,17-(di-$R_1$-oxycarbonyl)normorphinone enol acylate of Formula L (e.g., 3,17-(diethoxycarbonyl)normorphinone enol acetate) may be recovered from the reaction mixture in any suitable manner. Preferably, following completion of the reaction, the reaction mixture is cooled (preferably to about 25° C.), and recovery is effected employing an extraction procedure. Such extraction may be effected using an organic solvent which may be, for example, an arene, ketone, ester, chlorinated alkane or chlorinated arene capable of preferentially dissolving Compound L and thereafter evaporating the extract solvent to yield an oil. Chloroform is preferred for use as the extraction solvent. Preferably, the solvent extracted reaction mixture is washed with water, the resulting organic layer is dried by stirring over anhydrous sodium sulfate, followed by evaporation of the solvent to yield the oil, i.e., the desired compound L.

Step 4. In the next step of the process for preparing noroxymorphone from morphine, 14-hydroxy-3,17-(di-$R_1$-oxycarbonyl)normorphinone compound, Formula M, is prepared by reactively contacting the compound of Formula L with a peroxy oxidation agent capable of introducing a beta-oriented hydroxyl group in the 14 position. Such peroxy oxidation agent may be, for example, an aromatic or aliphatic, monobasic or polybasic carboxylic peracid. Suitable peracids include, for example, substituted or unsubstituted perbenzoic acids, wherein the substituent may be, for example, chloro, bromo, iodo, fluoro or nitro; monoperphthalic acid; performic acid; peracetic acid; monopermaleic acid; trifluoroperacetic acid; and trichloroperacetic acid. In chloro-, bromo-, iodo- and fluoroperbenzoic acids, the indicated halogen substituent is preferably in the meta position. The nitro group in nitroperbenzoic acid is preferably in the para position. The peracid is preferably chloroperbenzoic acid and more preferably is m-chloroperbenzoic acid.

The peracid may be formed in situ, that is, in the presence of the dienol acylate, by reaction of hydrogen peroxide with the corresponding acid or corresponding acid anhydride. Preferably, however, peracid is prepared prior to contacting it with the dienol acylate.

The act of reactively contacting the dienol acylate of Formula L with the peroxy oxidation agent is effected under Reaction Conditions effective for introducing or substituting a hydroxyl group in the 14 position of the dienol acylate such that the compound of Formula M is prepared. Preferably, the peroxy oxidation agent, sometimes referred to herein simply as the peracid or peroxyacid, is added to a solution or other mixture containing the dienol acylate in an inert organic solvent. That is, the organic solvent is a solvent for and substantially nonreactive with the 3,17-(di-$R_1$-oxycarbonyl) normorphinone enol acylate and the peracid. The solvent advantageously is present in a solubilizing amount for each of the dienol acylate and the peracid.

The organic solvent is preferably a polar organic solvent. Suitable classes of solvents include carboxylic acids, aprotic polar solvents, chlorinated hydrocarbons, carboxylic acid nitriles, carboxylic acid esters, ethers, mixtures thereof and the like. Carboxylic acids, aprotic polar solvents, chlorinated hydrocarbons and mixtures thereof are generally preferred. Suitable solvents include, for example, acetic acid, dimethylformamide, chloroform, methylene chloride (dichloromethane), acetonitrile, 1,2-dimethoxyethane, propyl acetate and mixtures thereof. Acetic acid is preferred, while glacial acetic acid is more preferred.

In addition to the solvent and the dienol acylate, the reaction mixture may include other components. For example, the reaction mixture may include agents effective for inhibiting formation of 7,8-epoxide derivatives of the dienol acylate and other side reaction products.

The reaction mixture preferably further includes, as an acid catalyst, an acid having a $pK_a$ of from about 0 to about 3 or slightly higher. It has surprisingly been found that inclusion of such acid permits preparation of the 14-hydroxy compound of Formula M in higher yield. Suitable acids include, for example, oxalic acid, trichloroacetic acid, trifluoroacetic acid, and methanesulfonic acid, as well as phosphoric acid, chloroacetic acid, maleic acid, and mixtures of two or more of such acids. Oxalic acid is preferred.

The reaction conditions preferably further include effecting the reaction of the dienol acylate with the peroxy oxidation agent in the substantial absence of water, i.e., with water not present in an amount greater than 5 percent by weight based on the weight of the reaction mixture. Water is preferably not present in an amount more than 2 percent, and more preferably not present in an amount more than 0.5 percent, on the same basis. Anhydrous reaction conditions are most preferred. Such anhydrous conditions result in higher yields than are generally attainable under aqueous conditions. Anhydrous reaction conditions may conveniently be provided by employing anhydrous components for the reaction mixture and conducting the reaction under an inert anhydrous atmosphere, e.g., dry nitrogen. Preferably, substantially no water of hydration is present in any of the components of the reaction mixture. Thus, for example, oxalic acid dihydrate may be converted to anhydrous oxalic acid by heating the dihydrate four hours at 100-110° C., followed by cooling in the presence of a dessicant in a dessicator or other air-tight container. Similarly, commercially available peracetic acid (usually containing 10-15% water) may be dried with $Na_2SO_4$ (e.g., 20 g per 100 ml) for several hours, decanting and drying at least 16 hours with 4A molecular sieves (e.g., 20 g per 100 ml). The peracid is preferably added as a solid. Normally liquid peracids (e.g., peracetic acid and performic acid) are preferably added as solutions thereof in an inert polar solvent, which may be, for example, methylene chloride or the parent or corresponding acid (e.g., acetic acid and formic acid for peracetic acid and performic acid, respectively).

The peracid is preferably added incrementally to the dienol acylate reaction mixture. The addition may advantageously be made in discrete portions, preferably four or five, and at an average rate of from about 0.01 to about 0.1 gram-equivalent per minute per mole of the dienol acylate. Desirably, a total of at least 1 gram-equivalent of the peracid is added per mole of the dienol acylate. The addition may advantageously be made over a period from about 30 to about 120 minutes, preferably with stirring of the reaction mixture.

The reaction may effectively be conducted at any suitable pressure (preferably about atmospheric pressure) and at any suitable temperature, e.g., about 10°–100° C., preferably about 15°–25° C.

The peracid may be added in a total amount of, for example, about 1 to 2.5 moles per mole of the dienol acylate, preferably from about 1.1 to about 1.4 moles and more preferably at about 1.4 moles on the same basis. The acid catalyst may be employed in an amount of, for example, about 0.01 to 0.5 mole, preferably about 0.5 mole, per mole of the dienol acylate. The solvent may be present in an amount of, for example, about 0.5 to 10 liters, preferably about 2.5 liters, per mole of the dienol acetate.

Where an acid catalyst is included in the reaction mixture, preferably the solvent is additionally a solvent for, and substantially nonreactive with, the acid catalyst and present in a solubilizing amount therefor.

At the completion of the reaction, the 14-hydroxy compound of Formula M can be conveniently recovered. Recovery can be effected readily by quenching the reaction mixture with water or preferably an aqueous alkali, for example, an aqueous solution of $NH_4OH$, NaOH, KOH, $NaHCO_3$, $NaH_2PO_4$, $Na_2HPO_4$ or a mixture of such alkalis. An aqueous mixture of NaOH and $NH_4OH$ is preferred. Thereafter, the 14-hydroxy compound can be separated by filtration of the quenched mixture, followed by extraction of the filtrate with a water-immiscible organic solvent, which may be, for example, an arene, ketone, ester, alcohol, chlorinated alkane, chlorinated arene, or a mixture of such solvents, provided that the solvent or mixture is capable of preferentially dissolving the compound of Formula M. It is preferably chloroform. This is followed by evaporation of the extraction solvent and drying of the resulting solid.

Although it is advantageous to cool the reaction mixture following completion of this reaction (as described above) and before the extraction procedure, such cooling can satisfactorily be omitted. Similarly, recovery of the compound of formula M can satisfactorily be omitted prior to hydrogenation (Step 5) which can proceed in situ in the reaction mixture of Step 4.

Step 5. In the next step of the process, 3,17-(diethoxycarbonyl)noroxymorphone is prepared from 14-hydroxy-3,17-(diethoxycarbonyl)normorphinone by reduction of this compound (Formula M), preferably by catalytic hydrogenation of that compound. Suitable catalysts include, for example, noble metal catalysts, which may be supported on a suitable support and may be chemically combined (e.g., platinum on carbon, palladium on carbon, rhodium on carbon, and platinum oxide). Charcoal-supported 5% palladium is preferred. It is used in an amount sufficient to provide about 0.1 part palladium per part of compound M.

The reduction reaction is preferably carried out in the presence of an inert organic liquid medium (hereinafter referred to as an "organic solvent") in which compound M can be dissolved or dispersed under the reaction conditions employed to form a solution, dispersion, suspension or other reaction mixture. The organic solvent employed in the reaction of Step 5 may be, for example, an alcohol (e.g., ethanol), an ester (e.g., ethyl acetate), or an acid (e.g., acetic acid or formic acid). The solvent is preferably glacial acetic acid.

Suitable conditions for the reaction in Step 5 include the addition or presence of, per mole of the compound of Formula M about 0.1–100 g of the catalyst employed (preferably about 45 g of 5% Pd on charcoal) and about 0.1–10 liters of an organic solvent (preferably about 3.9 liters of glacial acetic acid). The reaction may suitably be effected at, for example, about 1–10 atmospheres pressure, preferably about 3 atmospheres, of hydrogen, and a temperature of about 25°–80° C., preferably 25°–40° C., and more preferably about 40° C. The reaction can be completed within about 3 hours under the preferred conditions.

The product of Step 5, i.e., the compound of Formula N, can be recovered in any suitable manner. Recovery is preferably effected by filtering the reaction mixture through Celite diatomaceous earth to remove the catalyst; evaporating the solvent from the filtrate; dissolving the filtration residue in a mixture of 80% chloroform and 20% toluene, washing the resulting solution with water, adding to the resulting organic layer a sufficient amount of alkali (e.g., aqueous NaOH) with stirring and cooling to obtain a pH of about 8:5, removing the resulting aqueous layer, washing the residual organic phase with water, removing the washed organic phase and evaporating solvent therefrom; and combining the portions of the product thus recovered from the filtrate and from the filtration residue.

If the reaction of Step 5 was carried out in situ, i.e., without isolation of the product of Step 4, as described above, the recovery of the compound of Formula N as just described is preferably followed by a recovery step as set forth for Step 4 to remove the acid and acid catalyst present in the reaction mixture.

Step 6. In the next step of the process, noroxymorphone is prepared from 3,17-(diethoxycarbonyl) noroxymorphone (Formula N) by hydrolysis, preferably by contacting that compound with an acidic or basic hydrolysis catalyst preferably in the presence of water under hydrolytic conditions. This results in the corresponding hydrolysis-catalyst salt of noroxymorphone. Thereafter, noroxymorphone may be recovered by neutralizing the hydrolysis mixture with a neutralizing agent (for example, aqueous ammonium hydroxide), filtering the neutralized mixture, and washing and drying the filtrate.

Suitable acidic hydrolysis catalysts include, methane sulfonic acid, p-toluene sulfonic acid, trichloroacetic acid, hydrobromic acid (preferably in glacial acetic acid), hydrochloric acid (preferably in glacial acetic acid), mixtures of formic acid and strong acid (sometimes referred to as formic acid/strong acid), 20% hydrochloric acid, and mixtures of n-butanol/strong acid), and sulfuric acid. Suitable basic hydrolysis catalysts include, for example, potassium hydroxide, which may be employed as a solution thereof in ethanol, water, or diethylene glycol or the like. Sulfuric acid is the preferred catalyst.

Suitable conditions for the hydrolysis reaction using sulfuric acid include the addition of an amount of sulfuric acid (aqueous) corresponding to about 0.1-10 liters of 8N aqueous sulfuric acid per mole of the compound of Formula N. Preferably about 2 liters of 8N aqueous sulfuric acid on the same basis are used. Hydrolysis may suitably be effected at, for example, atmospheric pressure and a temperature of about 90°-100° C., preferably 100°-105° C. An inert atmosphere may be desirable when using sulfuric acid. Nitrogen is preferred.

The following examples are provided to illustrate the present invention, but are not meant to be limiting. All parts and percentages given through this disclosure are by weight unless otherwise indicated. Unless otherwise indicated, the identity of the compounds prepared in each example was confirmed by mass spectroscopy, IR and NMR (proton and carbon-13) and the reaction pressure in each example was approximately atmospheric.

EXAMPLE 1

Preparation of 3,17-(diethoxycarbonyl)normorphine from morphine (by Step 1)

A suspension of 60.6 g morphine.$H_2O$ in 600 ml toluene was refluxed under Dean-Stark conditions for 3 hours under nitrogen. Then the toluene was stripped under vacuum and 300 g potassium bicarbonate and 2000 ml chloroform were added. To the stirred mixture, 149 ml ethyl chloroformate was added slowly over 5 minutes. The resulting solution was refluxed for 6 hours under nitrogen; after cooling to 25° C., 1000 ml water was added to the stirred mixture, resulting in formation of an organic phase containing the product and an aqueous phase containing water-miscible solids which were removed from the reaction mixture by the water addition. The aqueous layer was removed and the organic phase was washed once with 200 ml water, dried over anhydrous sodium sulfate and concentrated. The solid obtained was recrystallized from ethyl acetate/hexane to give 78 g 3,17-(diethoxycarbonyl) normorphine, corresponding to a 94% yield.

EXAMPLE 2

Preparation of 3,17-(diethoxycarbonyl)normorphinone from 3,17-(diethoxycarbonyl)normorphine (by Step 2)

A solution of 50.1 q 3,17-(diethoxycarbonyl) normorphine (prepared substantially as set forth in Example 1) in 450 ml acetone was cooled to between 0°-10° C. under nitroqen. Then 46 ml of Jones Reagent (containing 13.2 g chromium trioxide, 12 ml concentrated sulfuric acid and 55 ml water) were added dropwise, while maintaining the temperature between 0°-10° C. At the end of the Jones Reagent addition, 20 ml isopropyl alcohol and 50 g solid sodium bicarbonate were added and the mixture was stirred for 30 minutes at 25° C. Next, the acetone solution was decanted and the residual solids were washed two times with 50 ml acetone and decanted. The decanted acetone solutions were combined and evaporated to give a yellow oil which crystallized from 2B anhydrous ethanol to give 33.5 g 3,17-(diethoxycarbonyl)normorphinone, which corresponds to 81% yield.

EXAMPLE 3

Preparation of 3,17-(diethoxycarbonyl)normorphinone enol acetate from 3,17-(diethoxycarbonyl)normorphinone (Step 3)

A mixture of 94 g 3,17-(diethoxycarbonyl)normorphinone (prepared substantially as set forth in Example 2), 18.7 g anhydrous sodium acetate and 430 ml acetic anhydride was heated at 100°-105° C. under nitrogen for 2 hours. The solution was cooled at 25° C., 500 ml chloroform were added and the organic mixture was washed two times with 100 ml water. The organic layer was dried thoroughly by stirring over anhydrous sodium sulfate for 30 minutes. Concentration of the resulting solution gave a dark brown oil assaying for 93 g of 3,17-(diethoxycarbonyl) normorphinone enol acetate, which corresponds to 90% yield.

EXAMPLE 4

Preparation of 14-hydroxy-3,17-(diethoxycarbonyl) normorphinone from 3,17-(diethoxycarbonyl)normorphinone enol acetate (Step 4)

Crude 3,17-(diethoxycarbonyl)normorphinone enol acetate (approximately 90 to 95% purity and prepared substantially as set forth in Example 3), containing 104 g pure compound and 9.5 g anhydrous oxalic acid were dissolved in 575 ml glacial acetic acid and cooled to 15° C. Then a total of 54.4 g m-chloroperbenzoic acid was added in five approximately equal portions at 10 minute intervals with stirring. After about 10-15 minutes following the final addition, the reaction mixture was poured into a mixture of 20 ml 50% NaOH, 800 ml NH$_4$OH and 800 g ice with stirring and the product was extracted with chloroform several times. The combined chloroform extracts were concentrated to give a residue assaying at 88 g 14-hydroxy-3,17-(diethoxycarbonyl)-normorphinone, which corresponds to 90% yield.

EXAMPLE 5

Preparation of 3,17-(diethoxycarbonyl)noroxymorphone from 14-hydroxy-3,17-(diethoxycarbonyl)normorphinone (Step 5)

A solution of 49 g 14-hydroxy-3,17-(diethoxycarbonyl)normorphinone (prepared substantially as set forth in Example 4) in 425 ml glacial acetic acid was added carefully to a hydrogenation bottle containing 5 g of 5% Pd on charcoal in 10 ml glacial acetic acid. The resulting mixture was shaken in a Parr apparatus under hydrogen atmosphere at 40° C. and a substantially constant reaction-chamber pressure of about 40 psig for 3 hours. After the hydrogenation reaction was substantially complete as indicated by HPLC monitoring of the reaction, the reaction mixture was cooled to about 25° C., the hydrogen supply was shut off, and the reaction chamber was flushed with nitrogen. Threafter, the catalyst was removed by filtration through Celite diatomaceous earth and the filtrate was concentrated. The residue was dissolved in 4:1 chloroform/toluene and washed two times with 50 ml water. The organic layer was stirred and cooled while adding 1N NaOH solution until a pH of 8.5 was reached. The aqueous layer was drawn off and the organic phase was washed two times with 100 ml water. Evaporation of solvents from the washed organic phase gave 49 g of 3,17-(diethoxycarbonyl)noroxymorphone as assayed by liquid chromatography, a 100% yield.

EXAMPLE 6

Preparation of noroxymorphone from 3,17-(diethoxycarbonyl)noroxymorphone (Step 6)

Crude 3,17-(diethoxycarbonyl)noroxymorphone (approximately 90 to 98% purity and prepared substantially as set forth in Example 5) containing 28 g pure compound was heated in contact with 128 ml 8N sulfuric acid solutiona at 100°–105° C. under nitrogen for 12 hours. The resulting solution was cooled to 25° C. and the sulfate salt of crude noroxymorphone was collected. The salt was dissolved in water and concentrated NCl was added to adjust the pH to 4.5; 2 g charcoal and 2 g filter aid were added and the resulting mixture was heated at 50° C. for 10 minutes. The hot mixture was filtered and after cooling to 25° C., the filtrate was adjusted to pH 8.8 to 9.0 with concentrated ammonium hydroxide, thereby precipitating noroxymorphone (a solid). The solid was filtered, washed with water and dried for 3 hours at 90° C. to give 12.5 g noroxymorphone at 90% assay, corresponding to 60% yield for Step 6.

The overall yield of noroxymorphone for the six steps of Examples 1-6 was 37% based on morphine.

In a large number of runs starting with 50 to 120 grams morphine, typical yields were 94–96% for Step 1 and 81–87% for Step 2.

EXAMPLE 7

Preparation of Noroxymorphone from 3,17-(diethoxycarbonyl)normorphinone

Step 3. A mixture of 26.9 g of 3,17-(diethoxycarbonyl)normorphinone (prepared in accordance with the procedure of Example 2), 5.3 g anhydrous sodium acetate and 122 ml acetic anhydride was heated at 100°–105° C. under nitrogen for 2 hours. The solution was cooled to 25° C., 140 ml chloroform were added, and the organic mixture was washed two times with 30 ml water. The organic layer was dried thoroughly by stirring over anhydrous sodium sulfate for 30 minutes. Concentration of the resulting solution gave a dark brown oil assaying for 26.5 g of 3,17-(diethoxycarbonyl)normorphinone enol acetate, which corresponds to 90% yield.

Step 4. The enol acetate oil and 2.7 g anhydrous oxalic acid were dissolved in 180 ml glacial acetic acid by adding the glacial acetic acid to the oil with stirring, followed by adding the oxalic acid with stirring. The resulting solution was cooled to 15° C. Then a total of 15.4 g m-chloroperbenzoic acid was added in approximately equal portions at 10 minute intervals with stirring. After about 10-15 minutes following the final addition, about 6 ml water was added and the resulting solution was stirred for about 30 minutes. At the end of such time, the solution assayed for 20.9 g 14-hydroxy-3-O,N-(diethoxycarbonyl)normorphinone, which corresponds to 84% yield for Step 4.

Step 5. To the solution of 20.9 g 14-hydroxy -3- O,N-(diethoxycarbonyl)normorphinone prepared in Step 4 was added sufficient glacial acetic acid, with stirring, to increase the volume of the solution to 230 ml. The resulting solution was added carefully to a hydrogenation bottle containing 27 g of 5% Pd on charcoal in 10 ml glacial acetic acid. The resulting mixture was shaken in a Parr apparatus under hydrogen atmosphere at 40° C. for 3 hours. The catalyst was removed by filtration through Celite diatomaceous earth and the filtrate was concentrated. The residue was dissolved in 4:1 chloroform/toluene and washed two times with 50 ml water. The organic layer was stirred and cooled while adding 1N NaOH solution until pH of 8.5 was reached. The aqueous layer was drawn off and the organic phase was washed two times with 50 ml water. Evaporation of solvents gave 20.0 g of 3,17-(diethoxycarbonyl)noroxymorphone, a 95% yield for Step 5, as assayed by liquid chromatography.

Step 6. Crude 3,17-(diethoxycarbonyl)noroxymorphone containing 20.0 g pure compound was heated with 128 ml 8N sulfuric acid solution at 100°–105° C. under nitrogen for 12 hours. The solution was cooled to 25° C. and the sulfate salt of crude noroxymorphone was collected. The salt was dissolved in water and concentrated HCl was added to adjust the pH to 4.5; 2 g charcoal and 2 g filter aid was added and heated at 50° C. for 10 minutes. The hot solution was filtered and after cooling to 25° C., the filtate was adjusted to pH 8.8-9.0 with concentrated ammonium hydroxide. The solid was filtered, washed with water and dried for 3 hours at 90° C. to give 11.1 g noroxymorphone, corresponding to 84% yield for Step 6.

The overall yield of noroxymorphone for the four steps of Example 7 was 60% based on the substituted morphine starting material. Taken with the typical yields set forth above for Steps 1 and 2, it is seen that noroxymorphone can be readily prepared from morphine in 46-50% or more overall yield based on morphine.

The following Examples illustrate use of the various peracid compounds for carrying out Step 4.

EXAMPLE 8

To 2.0 g powdered maleic anhydride in 8 ml methylene chloride cooled to 10° C. under nitrogen was added 0.5 g 67% hydrogen peroxide. The mixture was stirred at 10° for 15 min. Then a solution of 4.4 g 3,17-(diethoxycarbonyl)normorphinone enol acetate in 12 ml methylene chloride was added dropwise. The resulting solution was stirred at 10° for 1.5 hours. Then 0.5 ml water was added, followed by vigorous stirring for 15 minutes. The layers were allowed to separate and the aqueous phase was extracted two times with 25 ml methylene chloride. The combined organic layers were washed successively with 20 ml dilute sodium bicarbonate solution and 10 ml water. Then the organic layers were dried over anhydrous sodium sulfate and evaporated to give 3.5 g 14-hydroxy-3-O,N-(diethoxycarbonyl)normorphinone which corresponds to 85% yield.

EXAMPLE 9

To 1.3 ml trifluoroacetic anhydride in 4 ml methylene chloride cooled to 10° C. under nitrogen was added 0.25 g 67% hydrogen peroxide. The mixture was stirred at 10° for 15 min. Then a solution of 22 g 3,17-(diethoxycarbonyl)normorphinone enol acetate in 4 ml methylene chloride was added dropwise. The resulting solution was stirred at 10° for 2 hours. Then 0.5 ml water was added, followed by vigorous stirring for 15 minutes. The layers were allowed to separate and the aqueous phase was extracted two times with 25 ml methylene chloride. The combined organic layers were washed successively with 20 ml dilute sodium bicarbonate solution and 10 ml water. Then the organic layers were dried over anhydrous sodium sulfate and evaporated to give 0.88 g 14-hydroxy-3,17-(diethoxycarbonyl)normorphinone which corresponds to 43% yield. The same yield may be obtained if glacial acetic acid is used instead of methylene chloride.

EXAMPLE 10

A solution of 2.2 g 3,17-(diethoxycarbonyl) normorphinone enol acetate in 5 ml of glacial acetic acid was cooled to 20° C. under nitrogen. Then 0.25 g of 67% hydrogen peroxide was added dropwise and the solution was stirred at 90° C. for 2 hours. Then 5 ml water were added and the solution was extracted two times with 50 ml methylene chloride. The organic solution was washed with dilute sodium bicarbonate solution, dried over anhydrous sodium sulfate, and evaporated to give 0.78 g 14-hydroxy -3,17-(diethoxycarbonyl)normorphinone (38% yield).

EXAMPLE 11

A solution of 2.2 g 3,17-(diethoxycarbonyl) normorphinone enol acetate in 4 ml of 88% formic acid was cooled to 20° under nitrogen. Then 0.25 g of 67% hydrogen peroxide was added dropwise and the solution was stirred at 25° for 1 hour. Then 5 ml water were added and the solution was extracted two times with 50 ml methylene chloride. The organic solution was washed with dilute sodium bicarbonate solution, dried over anhydrous sodium sulfate, and evaporated to give 0.68 g 14-hydroxy-3,17-(diethoxycarbonyl)normorphinone (33% yield).

What is claimed is:

1. A process for preparing noroxymorphone from morphine comprising:
   (1) reacting morphine in a single step with a haloformate ester of the formula X—C(=O)OR$_1$, wherein X is halogen and R$_1$ is alkyl, so as to form 3,17-(di-R$_1$-oxycarbonyl)normorphine;
   (2) oxidizing the hydroxyl group of the 3,17-(di-R$_1$-oxycarbonyl)normophine with an oxidizing agent, under acidic conditions at a pH of less than 1.0, so as to form 3,17-(di-R$_1$-oxycarbonyl)normorphinone;
   (3) acylating the 3,17-(di-R$_1$-oxycarbonyl) normophinone with an acylating agent so as to form 3,17-(di-R$_1$-oxycarbonyl)normorphinone dienol acylate;
   (4) contacting the dienol acylate with a peroxy oxidation agent so as to introduce a beta-oriented hydroxyl group in position 14 of said dienol acylate, so as to form 14-hydroxy 3,17-(di-R$_1$-oxycarbonyl)-normorphinone;
   (5) hydrogenating the 14-hydroxy-3,17-(di-R$_1$-oxycarbonyl)normorphinone in a reduction reaction so as to form 3,17-(di-R$_1$-oxycarbonyl)noroxymorphinone; and
   (6) hydrolysing the 3,17-(di-R$_1$-oxycarbonyl) noroxymorphinone under hydrolytic conditions, so as to form noroxymorphone.

2. The process of claim 1 wherein R$_1$ is selected from the group consisting of methyl, ethyl, propyl, heptyl, and 1,1,1-trichloroethyl groups.

3. The process of calim 1 wherein R$_1$ is ethyl.

4. The process of claim 1 wherein the acylate is acetate.

5. 3,17-(di-R$_1$-oxycarbonyl)normorphinone wherein R$_1$ is an alkyl group.

6. The compound of claim 5 wherein R$_1$ is ethyl, whereby said compound is 3,17-(diethoxycarbonyl)-normorphinone.

7. 3,17-(di-R$_1$-oxycarbonyl)normorphinone dienol acylate wherein R$_1$ is an alkyl group.

8. The compound of claim 7 wherein the acylate is acetate, whereby the compound is 3,17-(di-R$_1$-oxycarbonyl)normorphinone dienol acetate.

9. The compound of claim 8 wherein R$_1$ is ethyl, whereby the compound is 3,17-(diethoxycarbonyl) normorphinone dienol acetate.

10. 14-hydroxy-3,17-(di-R$_1$-oxycarbonyl) normorphinone wherein R$_1$ is an alkyl group.

11. The compound of claim 10 wherein R$_1$ is ethyl, whereby the compound is 14-hydroxy-3,17-(diethoxycarbonyl)normorphinone.

12. A process for preparing the compound of claim 5, comprising reactively contacting 3,17-di-R$_1$-oxycarbonyl)normorphine, wherein R$_1$ is an alkyl group, under acidic conditions at a pH less than 1.0, with an oxidizing agent effective for oxidizing allylic hydroxyl group to keto groups.

13. The process of claim 12 wherein said oxidizing agent is chromium trioxide.

14. A process for preparing the compound of claim 10, comprising reactively contacting 3,17-(di-R$_1$-oxycarbonyl)normorphinone dienol acylate, wherein R$_1$ is an alkyl, alkenyl, aralkyl or aryl group, with an aromatic or aliphatic monobasic or polybasic peracid under reaction conditions effective for substituting a hydroxyl group in the 14 position of said compound.

15. The process of claim 14 wherein said peroxy acid is selected from the group consisting of substituted or unsubstituted perbenzoic acids wherein the substituent is selected from the group consisting of chloro, bromo, iodo, fluoro and nitro; monoperphthalic acid; performic acid; peracetic acid; monopermaleic acid; trifluoroperacetic acid; and trichloroperacetic acid.

16. The process of claim 14 wherein said reaction conditions include effecting said contacting
   (1) in the presence of
      (A) an acid catalyst having a pK$_c$ of from about 0 to about 3.0, and
      (B) a polar organic solvent which is a solvent for and substantially nonreactive with the 3,17-(di-R$_1$-oxycarbonyl)normorphinone enol acylate, said peracid and said acid catalyst; said solvent being present in a solubilizing amount for each of the 3,17-(di-R$_1$-oxycarbonyl)normorphinone enol acylate, said peracid and said acid catalyst;
   (2) in the substantial absence of water; and
   (3) with at least about 1 gram-equivalent of said peracid being present per gram-mole of the 3,17-(di-R$_1$-oxycarbonyl)normorphinone enol acylate.

17. The process of claim 16 wherein said acid catalyst is an acid selected from the group consisting of oxalic acid, trichloroacetic acid, trifluoroacetic acid, and methanesulfonic acid.

18. The process of claim 16 wherein said peracid is m-chloroperbenzoic acid, said acid catalyst is oxalic acid, and said solvent is glacial acetic acid.

* * * * *

UNITED STATES PATENT AND TRADEMARK OFFICE
CERTIFICATE OF CORRECTION

PATENT NO. : 5,112,975

DATED : May 12, 1992

INVENTOR(S) : Rebecca A. Wallace

It is certified that error appears in the above-identified patent and that said Letters Patent is hereby corrected as shown below:

Col. 1, line 6, "agan" should be --aban--.

Col. 9, line 14, "advantaqeous1Y" should be --advantageously--.

Col. 13, line 17, "NCl" should be --HCl--.

Col. 14, line 21, "adjust" should be --adjust--.

Signed and Sealed this

Sixteenth Day of November, 1993

Attest:

BRUCE LEHMAN

*Attesting Officer*   *Commissioner of Patents and Trademarks*